United States Patent [19]

Horodysky et al.

[11] Patent Number: 5,348,671
[45] Date of Patent: Sep. 20, 1994

[54] LUBRICANT COMPOSITIONS CONTAINING ARYLSULFONIC ACIDS, AND ORGANO PHOSPHITES AND REACTION PRODUCTS THEREOF

[75] Inventors: Andrew G. Horodysky, Cherry Hill, N.J.; Derek A. Law, Yardley; Shi-Ming Wu, Newtown, both of Pa.

[73] Assignee: Mobil Oil Corporation, Fairfax, Va.

[21] Appl. No.: 7,904

[22] Filed: Jan. 22, 1993

Related U.S. Application Data

[63] Continuation-in-part of Ser. No. 771,281, Oct. 3, 1991, abandoned, which is a continuation-in-part of Ser. No. 471,913, Jan. 29, 1990, abandoned, which is a continuation-in-part of Ser. No. 292,800, Jan. 3, 1989, Pat. No. 4,897,209.

[51] Int. Cl.$^5$ ................. C10M 135/10; C10M 137/04
[52] U.S. Cl. ................. 252/32.7 E; 252/32.5; 252/46.6; 558/218
[58] Field of Search ................. 252/46.6, 33.3, 32.7 E, 252/32.7 R, 32.5; 558/218

[56] References Cited

U.S. PATENT DOCUMENTS

| | | | |
|---|---|---|---|
| 2,764,548 | 9/1956 | King et al. | 252/33 |
| 3,082,187 | 3/1963 | Fushman et al. | 558/218 |
| 3,459,662 | 8/1969 | Shih-en-hu | 252/46.6 |
| 3,627,681 | 12/1971 | William | 252/32.7 E |
| 4,130,494 | 12/1984 | Shaub et al. | 252/33 |
| 4,177,192 | 12/1979 | Heiba et al. | 252/33 |
| 4,328,111 | 5/1982 | Watson | 252/32.5 |
| 4,349,445 | 9/1982 | Rosenberger | 558/86 |
| 4,419,251 | 12/1983 | Shim et al. | 252/32.7 |
| 4,419,252 | 12/1983 | Shim et al. | 252/32.7 |
| 4,626,368 | 12/1986 | Cardis | 252/49.9 |
| 4,717,491 | 1/1988 | Cardis | 252/46.7 |
| 4,814,097 | 3/1989 | Cardis | 252/46.6 |
| 4,897,209 | 1/1990 | Law et al. | 252/32.7 E |
| 4,992,184 | 2/1991 | Harodysky et al. | 252/32.7 E |

*Primary Examiner*—Margaret Medley
*Attorney, Agent, or Firm*—Alexander J. McKillop; Dennis P. Santini; Robert B. Furr, Jr.

[57] ABSTRACT

Disclosed are lubricant compositions containing a lubricant and: (a) the reaction product of a non-metallic dihydrocarbylaromatic or monohydrocarbylaromatic sulfonate and a dialkyl or trialkyl phosphite; or (b) the reaction product of a non-metallic dialkylnaphthalene sulfonate and a dialkyl or trialkyl phosphite and further containing an acid or acid supplying component; or (c) an unreacted mixture of dialkylnaphthalene sulfonic acid and a dialkyl or trialkyl phosphite.

12 Claims, No Drawings

LUBRICANT COMPOSITIONS CONTAINING ARYLSULFONIC ACIDS, AND ORGANO PHOSPHITES AND REACTION PRODUCTS THEREOF

CROSS-REFERENCE TO RELATED APPLICATIONS

This application is a continuation-in-part of application Ser. No. 07/771,281, filed Oct. 3, 1991, now abandoned, which is a continuation-in-part of application Ser. No. 07/471,913 filed Jan. 29, 1990 (now abandoned) which is a continuation-in-part of application Ser. No. 292,800, filed Jan. 3, 1989, now U.S. Pat. No. 4,897,209.

NATURE OF THE INVENTION

This invention relates to lubricants and particularly to lubricants containing or generating arylsulfonic acids, organo phosphites and the reaction products of aryl sulfonic acids and organophosphites.

BACKGROUND

Calcium sulfonate is a known rust inhibitor and demulsifier additive for lubricating oils and greases. U.S. Pat. Nos. 4,419,251 and 4,419,252 disclose calcium dinonyl naphthalene sulfonate as a component for a lubricant concentrate for forming oil-in-water emulsions upon dilution with water. Organophosphites have been used for their extreme pressure and antiwear properties in lubricant formulations. U.S. Pat. Nos. 4,717,491 and 4,626,368 discloses the use of reaction products of dialkyl and trialkyl phosphites in lubricant compositions.

U.S. Pat. No. 4,897,209 to Law and Wu teaches lubricant compositions containing a lubricant and:
(a) the reaction product of a metal dihydrocarbylaromatic sulfonate and a dialkyl or trialkyl phosphite; or
(b) the reaction product of a metal dialkylnaphthalene sulfonate and a dialkyl or trialkyl phosphite and further containing an acid or acid supplying component; or
(c) an unreacted mixture of dialkylnaphthalene sulfonic acid and a dialkyl or trialkyl phosphite.

SUMMARY OF THE INVENTION

This invention comprises in one aspect a lubricant composition containing (a) the reaction product of a non-metallic dihydrocarbylaromatic or monohydrocarbylaromatic sulfonate such as a non-metallic dialkylnaphthalene sulfonate and a dihydrocarbyl or trihydrocarbyl phosphite, such as dialkyl or trialkyl phosphite, or (b) the reaction product of a non-metallic dihydrocarbyl- or monohydrocarbyl-sulfonic acid, such as a non-metallic dialkylnaphthalene sulfonate or dihydrocarbyl or trihydrocarbyl phosphite, such as dialkyl or trialkyl phosphite and further containing an acid or acid supplying component, or (c) a dihydrocarbyl or monohydrocarbyl aromatic sulfonic acid, such as dialkylnaphthalene sulfonic acid and a dihydrocarbyl or trihydrocarbyl phosphite. Another aspect of this invention comprises the method of making the lubricant composition by incorporating any of the above described groups into a lubricant.

Still another aspect of this invention comprises the reaction product of non-metallic dialkylnaphthalene or monoalkyl- or mono- or dihydrocarbyl sulfonate or dialkylnaphthalene or monoalkyl- or mono- or dihydrocarbyl sulfonic acid and a dialkyl or trialkyl phosphite or dihydrocarbyl or trihydrocarbyl phosphite.

Lubricants containing the additives of this invention have unusually high thermal stability and dispersancy in comparison with lubricants containing the metal-containing additives taught in U.S. Pat. No. 4,897,209 to Law and Wu, cited above.

DETAILED DESCRIPTION OF THE INVENTION (a) Reaction Product of Non-Metallic Dihydrocarbyl- or Monohydrocarbyl-Aromatic such as Non-Metallic Dialkylnaphthalene Sulfonate and Dihydrocarbyl or Trihydrocarbyl Phosphite The non-metallic dialkylnaphthalene sulfonate has a sulfonate group attached to one ring of the naphthalene nucleus and one or more hydrocarbyl groups attached to one or both rings. One or both hydrocarbyl groups can independently contain from about six to about twenty carbon atoms, but it is preferred that they contain from about eight to twelve carbon atoms. The mono- or dihydrocarbylnaphthalene sulfonate group is attached to a nitrogen moiety through the sulfonate group. For ammonium, amines or alkanolamine salts, one dialkylnaphthalene sulfonate group is attached to each nitrogen atom while there are two groups attached to each nitrogen atom of a polyalkenylene diamine. Alkoxylated monoamines or diamines can also be used as well as diaryl amines and aryl diamines, such as phenyldiamines. Polyalkenylene diamines include ethylene, trimethylene, tetramethylene, pentamethylene, hexamethylene and up to $C_{20}$ terminal diamine, or etheral diamines prepared from fatty alcohols and acrylonitrile, then reduced with hydrogenation where the fatty alcohol may have from 1 to 30 carbon atoms, with 6 to 20 carbon atoms being preferred. While polyalkenylene diamines or etheral diamines can be used to link the sulfonate, ethylene diamine is the preferred terminal diamine.

The dihydrocarbyl or trihydrocarbyl phosphite has the general formula:

$$(R_1O)_2POR_2$$

where $R_1$ is a hydrocarbon radical of 1 to 18 carbon atoms, preferably 4 to 18 carbon atoms, and $R_2$ is hydrogen or a hydrocarbon radical of 1 to 18 carbon atoms preferably 4 to 18 carbon atoms. Useful hydrocarbyl phosphites include oleyl, phenyl, nonyl phenyl, octylphenyl, 2-ethyl hexyl, 1,3-dimethylbutyl, tridecyl, isodecyl, octyl and butyl, and mixed phosphites of the above radicals. Trihydrocarbyl phosphites are often preferred over dihydrocarbyl phosphites. If desirable, an unreactive organic solvent can be utilized. Preferably the organic solvent is selected from benzene, toluene, xylene, and mixed alkyl and aromatic petroleum distillates.

In preparing the reaction product of the non-metallic mono- or dialkylnaphthalene sulfonate and hydrocarbyl phosphite the two materials preferably are reacted at a temperature between 30° C. and 250° C., more preferably from 60° C. to 160° C. in a molar ratio of from 10:1 to 1:10 moles of sulfonate per mole of phosphite.

The reaction product thus obtained is added to the base lubricating oil stock in a concentration of between 0.01% and 10%.

(b) Reaction Product of Non-metallic Dihydrocarbyl- or Monohydrocarbyl Aromatic Sulfonates, such as Dialkylnaphthalene Sulfonate and Di- or Trihydrocarbyl Phosphite such as Di- or Trialkyl Phosphite and an Acid or Acid-Supplying Component The reaction product is prepared as described in (a) above and is added to the base lubricating oil along with an acid or acid source. The usable acids or acid sources include dilute sulfuric acid, as well as any other source of inorganic or organic acids such as fatty acids capable of generating proton-derived acidity. The reaction product and acid source are each added to the lube oil base stock in concentrations of 0.01% to 10% and 0.001% to 1% respectively.

(c) Unreacted Mono- or Dihydrocarbylaromatic such as Dihydrocarbyl Dialkylnaphthalene or Monoalkylnaphthalene Sulfonic Acid and Di- or Trihydrocarbyl Phosphite Added to Base Oil In this modification of the invention the dihydrocarbylaromatic or monohydrocarbylaromatic sulfonic acid, such as dialkylnaphthalene sulfonic acid, or monoalkylnaphthalene sulfonic acid and the di- or trialkyl phosphite components are not reacted but are combined directly into the lubricating oil composition and make use of acids generated during oil degradation in service. The concentration of each in the lube oil compositions is between 0.01% and 5% and between 0.01% to 5% respectively.

An important feature of the invention is the ability of the additive to improve the antiwear properties and the resistance to oxidation of a lubricating oil such as mineral oil, synthetic oils, mixtures of these, or a grease in which any of the aforementioned oils are employed as a vehicle. Lubricants containing the non-metallic additives of the present invention exhibit unusually high thermal stability and dispersancy in comparison with lubricants containing the metallic additives of U.S. Pat. No. 4,897,209 to Law and Wu, cited above. In general, the mineral oils, both paraffinic, naphthenic and mixtures thereof, employed as a lubricating oil or as the grease vehicle, can be of any suitable lubricating viscosity range, as for example, from about 45 SSU at 100° F. to about 6000 SSU at 100° F., and preferably from about 50 to about 250 SSU at 210° F. These oils may have viscosity indexes ranging to 100 or higher. Viscosity indexes from about 70 to about 95 are preferred. The average molecular weights of these oils can range from about 250 to about 800.

Where the lubricant is employed as a grease, the lubricating oil is generally used in an amount sufficient to balance the total grease composition, after accounting for the desired quantity of the thickening agent, and other additive components included in the grease formulation. A wide variety of materials can be employed as thickening or gelling agents. These can include any of the conventional metal salts or soaps, such as calcium, or lithium stearates or hydroxystearates, which are dispersed in the lubricating vehicle in grease-forming quantities in an amount to impart to the resulting grease composition the desired consistency. Other thickening agents that can be employed in the grease formulation comprise the non-soap thickeners, such as surface-modified clays and silicas, aryl ureas, calcium complexes and similar materials. In general, grease thickeners can be employed which do not melt and dissolve when used at the required temperature within a particular environment; however, in all other respects, any material which is normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in preference to mixtures of mineral and synthetic oils, various synthetic oils may be utilized successfully. Typical synthetic oil vehicles include polyisobutylenes, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes) and alkyl-substituted diphenyl ethers typified by a butyl-substituted bis(p-phenoxy phenyl) ether, and phenoxy phenylethers.

It is to be understood that the compositions contemplated herein can also contain other materials. For example, other corrosion inhibitors, extreme pressure agents, viscosity index improvers, coantioxidants, antiwear agents and the like can be used. These include, but are not limited to, phenates, sulfonates, succinimides, zinc dialkyl or diaryl dithiophosphates, and the like. These materials do not detract from the value of the compositions of this invention.

The products of this invention can also be employed in liquid hydrocarbon fuels, alcohol fuels or mixtures thereof, including mixtures of hydrocarbons, mixtures of alcohols and mixtures of hydrocarbon and alcohol fuels. Liquid hydrocarbon fuels include gasoline, fuel oils, diesel oils, and alcohol fuels such as methyl and ethyl alcohols.

EXAMPLE 1

Approximately 92.3 grams of calcium dinonylnaphthalene sulfonate commercially obtained from King Industries, Inc., as Na-Sul 729 was charged to a flask equipped with thermometer, nitrogen gas sparger, condenser, and agitator and diluted with 100 ml of toluene. Tributyl phosphite (12.5 grams, 0.05 mol) was then added at room temperature, and the reaction mixture was heated to reflux for 4 hours. The resulting product was evaporated under a reduced pressure at 110° C. resulting in a yield of 96.5 grams of viscous dark brown fluid.

EXAMPLE 2

Approximately 112 grams of the dinonylnaphthalene sulfonate described in Example 1 was mixed in 50 ml of toluene and acidified with 4.9 ml of 30% sulfuric acid under a nitrogen atmosphere. The mixture was heated to 60° C. for two hours and then cooled to room temperature. Tributyl phosphite (15.3 grams, 0.06 mole) was added dropwise; the reaction was slightly exothermic (from 25° C. to 31° C.), and at the end of the addition, the mixture was heated to reflux for 3 hours. The resulting mixture was diluted with 250 ml of toluene and washed with water, dried, and evaporated under a reduced pressure at 110° C. to yield 133 grams of a viscous grey-brown fluid.

EXAMPLE 3

Approximately 112 grams of the previously described sulfonate mixed in 50 ml of toluene was acidified with 4.9 ml of 30% sulfuric acid. After one hour of reaction time at 60° C. dibutyl phosphite (11.9 grams, 0.6 mole) was added dropwise, and the reaction mixtures was then heated to reflux for 3 hours. The resulting mixture was filtered, washed with toluene, and the combined filtrate and washings evaporated under a reduced pressure at 110° C. to yield 123 grams of viscous brown fluid.

COMPARATIVE EXAMPLE A

Approximately 95.4 g of ammonium dinonylnaphthalene sulfonate (commercially obtained from King Industries, Inc. as Na-Sul AS) was charged to a one liter, 4-neck flask (equipped with thermometer, $N_2$ sparger, condenser, and agitator) and diluted with 50 ml of toluene. Tributyl phosphite (25 g, 0.10 mol) was then added at room temperature, and the reaction mixture was heated to reflux for four hours. The resulting product was evaporated under vacuum at 130° to yield 130 g of viscous brown fluid.

COMPARATIVE EXAMPLE B

Approximately 95.4 g of Na-Sul AS as described in Example A in 50 ml of Toluene was acidified with 8 ml of 30% sulfuric acid under $N_2$ atmosphere. The mixture was heated to 60° for two hours and then tributyl phosphite (25 g, 0.10 mol) was added as a gentle stream. The reaction mixture was heated to reflux for three hours. The resulting reaction mixture was filtered (4.0 g of ammonium sulfate was obtained), the filtrate was washed with water (2×30 ml), dried and evaporated under vacuum at 130° to yield 114 g of dark brown fluid.

COMPARATIVE EXAMPLE C

Approximately 95.4 g of Na-Sul AS as described in Example A in 50 ml of toluene was acidified with 8 ml of 30% sulfuric acid under $N_2$ atmosphere. The mixture was heated to 60° C. for two hours, then dibutyl phosphite (19.4 g, 0.10 mol), was added and further reacted for three hours at reflux, The resulting reaction mixture was filtered (4.0 g. of ammonium sulfate was obtained), the filtrate was washed with water (2×30ml), dried and evaporated under vacuum at 130° C. to yield 108 g of dark brown fluid.

Evaluation of Products

The products of the Examples were blended into solvent paraffinic neutral mineral oil and evaluated for testing oxidative stability. Results are reported in Tables 1–3. The EP/antiwear properties are shown in Tables 3 and 4. Tables 1–3 illustrate the antioxidant characteristics of the Examples.

TABLE 1

| Item | Catalytic Oxidation Test 325° F., 40 hours | |
|---|---|---|
| | Increase in Acidity Change in Acid Number Δ TAN | Viscosity Increase Percent Change in Kinematic Viscosity Δ KV % |
| Base oil (100% solvent paraffinic neutral mineral oil) | 6.63 | 66.3 |
| 1% of example 1 | 0.50 | 6.2 |
| 1% of example 2 | 0.34 | 6.1 |
| 1% of example 3 | −0.15 | 4.1 |

TAN = Total Acid Number

TABLE 2

| Item | Catalytic Oxidation Test 325° F., 72 hours | |
|---|---|---|
| | Increase in Acidity Change in Acid Number, Δ TAN | Viscosity Increase Percent Change in Kinematic Viscosity, Δ KV, % |
| Base oil (100% solvent paraffinic neutral mineral oil) | 8.16 | 110.0 |
| 1% of example 1 | 1.49 | 10.4 |
| 1% of example 2 | 0.73 | 17.9 |
| 1% of example 3 | 0.09 | 14.2 |

TABLE 3

| Item | Catalytic Oxidation Test 325° 40 HOURS | |
|---|---|---|
| | Increase in Acidity Change in Acid Δ TAN | Viscosity Increase Percent Change in Kinematic Viscosity, Δ KV % |
| Base oil (100% solvent paraffinic neutral mineral oil) | 16.58 | 220.6 |
| 1% of Comparative Example A in above base oil | 14.49 | 670.7 |
| 1% of Comparative Example B in above base oil | 15.04 | 151.3 |
| 1% of Comparative Example C in above base oil | 0.69 | 9.8 |

TABLE 4

| Item | Four Ball Wear Test Wear Scar Diameter in mm, 30 minute test, 60 kg Load, 2000 RPM, 200° F. |
|---|---|
| Base oil (80% solvent paraffine bright; 20% solvent paraffinic neutral mineral oils) | 2.03 |
| 1% Na-Sul AS + 1% (BuO)$_3$P in above base oil (ingredients not previously reacted but merely blended into base oil) | 2.24 |
| 1% Na-Sul AS + 1% (BuO)$_3$P + 0.2% H$_2$SO$_4$ in above base oil (ingredeints not previously reacted but merely blended into base oil) | 0.43 |
| 1% Na-Sul AS + 1% (BuO)$_3$P + 1% H$_2$SO$_4$ in above base oil (ingredients not previously reacted but merely blended into base oil) | 0.68 |
| 1% of Comparative Example A | 1.97 |

TABLE 4-continued

| Item | Four Ball Wear Test Wear Scar Diameter in mm, 30 minute test, 60 kg Load, 2000 RPM, 200° F. |
|---|---|
| in above base oil | |
| 1% of Comparative Example B in above base oil | 0.46 |
| 1% of Comparative Example C in above base oil | 0.98 |

The results shown in Table 4 clearly illustrate the improvement in antiwear properties of item 2 sulfonate/phosphite mixture when acidified during test operation as shown in items 3 and 4 exhibiting much less wear than non-acidified mixture. The wear scar diameter decreased from 2.24 mm to as low as 0.43 mm via the in-situ neutralization technique.

Table 4 also illustrates the antiwear properties of the products of Comparative Examples A, B, and C pre-acidified in the laboratory prior to measurement of antiwear properties.

Hot Tube Testing

Results of "Hot Tube Tests" clearly demonstrate that additives prepared from the reactions of non-metallic sulfonates with organo phosphites have better thermal/oxidative stability and dispersancy than the metallic sulfonates with organo phosphites as taught in U.S. Pat. No. 4,897,209 to Law and Wu.

The additives were blended into synthetic engine oil without dispersant, these blended oils were passed through an aluminum heating block via capillary pyrex tube, with a flow rate of 0.35 ml per hour and 10.0 cc/min of air feed rate, the temperature of aluminum block was maintained at 295° for a total period of 16 hrs. These capillary pyrex tubes were flushed with hexanes to remove oil but not lacquer and carbon deposits, and rated for lacquer and carbon deposits.

A rating scale from 1 to 9 is used, with 1 being clean and 9 being a heavy black carbon deposit. Ratings are assigned by comparison with reference standards.

TABLE 5

Hot Tube Test
295° C./16 hrs. 0.35 cc/hr flow rate, 10.0 cc/min air rate

| Item | Rating |
|---|---|
| Synthetic engine oil with metallic detergents but without dispersant (as reference oil) | 9 |
| 2% of the reaction product of Comparative Example A in above oil (reaction product of Na-Sul AS and tributyl phosphite) | 2 |
| 2% of the reaction product of Example 1 (also Example 1 of U.S. Pat. No. 4,847,209, the reaction product of Na-Sul 729 and tributyl phosphite) | 6 |

Results of the Hot Tube Test show that the nonmetallic additives of the present invention have superior thermal/oxidation stability and dispersancy to the metallic additives taught in U.S. Pat. No. 4,897,209 to Law and Wu.

Changes and modifications in the specifically described embodiments can be carried out without departing from the scope of the invention which is intended to be limited only by the scope of the appended claims.

What is claimed is:

1. An additive composition for lubricating oils comprising an inorganic acid and a reaction product resulting from reacting a non-metallic dihydrocarbylaromatic sulfonate compound having a nitrogen containing moiety selected from the group consisting of alkanolamine salts, polyalkenylene diamines, etheral diamines, aryldiamines, diaryldiamines, and alkylated diamines or a monohydrocarbylaromatic sulfonate compound having a nitrogen containing moiety selected from the group consisting of ammonium, amines, alkanolamine salts, and alkylated amines and a dihydrocarbyl or trihydrocarbyl phosphite in a mole ratio of sulfonate compound to phosphite compound of between about 10:1 and about 1:10 at a temperature between about 60° C. and about 200°.

2. The additive composition of claim 1 wherein the non-metallic dialkylnaphthalene sulfonate compound is an ammonium salt.

3. The additive composition of claim 1 wherein the non-metallic dihydrocarbylaromatic sulfonate compound is ammonium dinonylnaphthalene sulfonate.

4. The additive composition of claim 1 wherein the dihydrocarbyl or trihydrocarbyl phosphite has the structural formula $(R_1O)_2POR_2$ where $R_1$ is a hydrocarbon radical of 1 to 18 carbon atoms and $R_2$ is hydrogen or a hydrocarbon radical of 1 to 18 carbon atoms.

5. The additive composition of claim 1 wherein the dihydrocarbyl or trihydrocarbyl phosphite is selected from the group consisting of oleyl, phenyl, nonyl phenyl, octylphenyl, 2-ethyl hexyl, 1,3-dimethylbutyl, tridecyl, isodecyl, octyl, and butyl, and mixed phosphites thereof.

6. The additive composition of claim 1 wherein the acid is sulfuric acid.

7. A lubricant composition comprising a hydrocarbon lubricant and between about 0.01% and about 10% by weight of the total composition of the reaction product of claim 1.

8. A lubricant composition comprising a hydrocarbon lubricant and between about 0.01% and about 10% by weight of the total composition of the reaction product of claim 2.

9. A lubricant composition comprising a hydrocarbon lubricant and between about 0.01% and about 10% by weight of the total composition of the reaction product of claim 3.

10. A lubricant composition comprising a hydrocarbon lubricant and between about 0.01% and about 10% by weight of the total composition of the reaction product of claim 5.

11. A lubricant composition comprising a hydrocarbon lubricant and between about 0.01% and about 10% by weight of the total composition of the reaction product of claim 6.

12. A method for making a lubricant composition comprising adding to a hydrocarbon lubricant between about 0.01% and about 10% by weight of the total composition of the additive composition of claim 3.

* * * * *